United States Patent [19]

Peck et al.

[11] Patent Number: 5,432,166

[45] Date of Patent: Jul. 11, 1995

[54] USE OF 1-(β-D-ARABINOFURANOSYL)-5-PROPYNYLURACIL FOR LOWERING SERUM CHOLESTEROL

[75] Inventors: Richard W. Peck; John Posner; Kenneth Powell, all of Beckenham, England

[73] Assignee: Burroughs Wellcome Co., Research Triangle Park, N.C.

[21] Appl. No.: 988,122

[22] PCT Filed: May 29, 1992

[86] PCT No.: PCT/GB92/00971

§ 371 Date: Feb. 11, 1993

§ 102(e) Date: Feb. 11, 1993

[87] PCT Pub. No.: WO92/21352

PCT Pub. Date: Dec. 10, 1992

[30] Foreign Application Priority Data

May 30, 1991 [GB] United Kingdom ............ 9111580

[51] Int. Cl.⁶ ................. A61K 31/70; C07H 19/09
[52] U.S. Cl. ..................... 514/50; 514/51; 536/28.54
[58] Field of Search .............. 514/50; 536/38.54

[56] References Cited

U.S. PATENT DOCUMENTS

| | | | |
|---|---|---|---|
| 4,594,339 | 6/1986 | Lopez et al. | 514/42 |
| 4,962,194 | 10/1990 | Bridges | 536/26 |
| 5,028,596 | 7/1991 | Purifoy et al. | 536/28.54 |
| 5,063,233 | 11/1991 | Chen et al. | 514/266 |

FOREIGN PATENT DOCUMENTS

| | | |
|---|---|---|
| 0175325 | 3/1986 | European Pat. Off. . |
| 0272065 | 12/1987 | European Pat. Off. . |
| 0277917 | 8/1988 | European Pat. Off. . |
| 0322242 | 12/1988 | European Pat. Off. . |
| 0354180 | 2/1990 | European Pat. Off. . |
| 0469968 | 2/1992 | European Pat. Off. . |
| 6509 | 6/1967 | France . |
| 2244328 | 9/1972 | Germany . |
| 47-026515 | 7/1972 | Japan . |
| 3287537 | 12/1991 | Japan . |
| 2199036 | 12/1987 | United Kingdom . |
| 2226027 | 11/1989 | United Kingdom . |

OTHER PUBLICATIONS

Eur. J. Med. Chem., Chim, Ther., (1980), 15 (1), 23–27.
Gaggi et al, Farmaco, Ed. Sci., (1980), 35 (7), 581–589.
de Clerq et al, J. Med. Chem. (1983), 26, 661–666.

Primary Examiner—Douglas W. Robinson
Assistant Examiner—Gary L. Kunz
Attorney, Agent, or Firm—Donald Brown; Lawrence A. Nielsen

[57] ABSTRACT

The use of 1-(β-D-arabinofuranosyl)-5-propynyluracil or a pharmaceutically acceptable salt or physiologically labile ester thereof for lowering serum cholesterol, particularly low density lipoprotein cholesterol levels in a human subject.

2 Claims, No Drawings

USE OF 1-(β-D-ARABINOFURANOSYL) -5-PROPYNYLURACIL FOR LOWERING SERUM CHOLESTEROL

The present invention relates to a new therapeutic use for a 5-substituted pyrimidine nucleoside.

1-(β-D-arabinofuranosyl)-5-propynyluracil is already known as an anti-viral agent having activity against viruses of the herpes group, in particular Varicella Zoster virus and cytomegalovirus. In this connection reference can be made to EP-A-0 417 560.

The role of elevated serum cholesterol levels in many pathological conditions in man is now well established and deposits of cholesterol in the vascular system have been implicated as causative of a number of pathological conditions such as coronary heart disease. Cholesterol is found in the blood in the form of complex particles which generally consist of a core of cholesterol esters and triglyceride surrounded by phospholipid and protein. Cholesterol is carried to sites where it is deposited in blood vessels in the form of so-called low density lipoprotein (LDL) cholesterol and is removed from such sites in the form of so-called high density lipoprotein (HDL) cholesterol.

It has now surprisingly been found that 1(β-D-arabinofuranosyl)-5-propynyluracil is effective in lowering serum cholesterol, and particularly LDL cholesterol, levels in cynomolgus monkeys and preliminary studies indicate a similar effect in human subjects.

Accordingly, the present invention provides a method for lowering serum cholesterol, particularly LDL cholesterol, levels in a human subject which comprises administering to the said subject an effective amount of 1-(β-D-arabinofuranosyl)-5-propynyluracil or a pharmaceutically acceptable salt or physiologically labile ester thereof.

Examples of clinical conditions which may be treated in accordance with the present invention include polygenic hypercholesterolaemia, familial hypercholesterolaemia, LDL receptor deficiency/abnormality, apoB deficiency/abnormality, familial combined hyperlipidaemia, apoE2 homozygosity, apoC2 deficiency and familial lipoprotein lipase deficiency.

The present invention also provides the use of 1(β-D-arabinofuranosyl) -5-propynyluracil or a pharmaceutically acceptable salt or physiologically labile ester thereof for the manufacture of a medicament for lowering serum cholesterol, particularly LDL cholesterol, levels in a human subject.

The present invention also provides a pharmaceutical composition for lowering serum cholesterol, particularly LDL cholesterol, levels in a human subject, which comprises 1(β-D-arabinofuranosyl)-5-propynyluracil or a pharmaceutically acceptable salt or physiologically labile ester thereof, together with at least one pharmaceutically acceptable carrier or diluent.

1(β-D-arabinofuranosyl)-5-propynyluracil, pharmaceutically acceptable salts and physiologically labile esters thereof, are known compounds and may be prepared by the methods described in EP-A-0 417,560. Suitable pharmaceutically acceptable salts for use according to the invention include salts formed with physiologically acceptable bases, for example alkali metal (e.g. sodium), alkaline earth metal (e.g. magnesium), ammonium and $NX_4^+$ (where X is for example $C_{1-4}$alkyl) salts. Pharmaceutically acceptable salts of 1(β-D-arabinofuranosyl) -5-propynyluracil may be prepared in conventional manner, for example by reaction of 1(β-D-arabinofuranosyl)-5-propynyluracil with the appropriate base.

As used herein, the term "physiologically labile ester" refers to an ester of 1-(β-D-arabinofuranosyl)-5-propynyluracil which upon administration to a human subject is converted to 1(β-D-arabinofuranosyl) -5-propynyluracil or a metabolite thereof having the same or similar cholesterol lowering activity to the parent compound. Examples of suitable mono- and di-esters include carboxylic acid esters in which the non-carbonyl moiety of the ester grouping is selected from straight or branched chain alkyl, alkoxyalkyl, carboxyalkyl, aralkyl, aryloxyalkyl and aryl (including aryl substituted by a substituent such as halogen, $C_{1-4}$alkyl or $C_{1-4}$alkoxy); sulphonate esters such as alkyl- and arylalkylsulphonyl; mono- di- and tri-phosphate esters, which may or may not be blocked; amino acid esters; and nitrate esters. Any reference to an ester also includes that ester in the form of a pharmaceutically acceptable salt.

1-(β-D-arabinofuranosyl)-5-propynyluracil or a pharmaceutically acceptable salt of physiologically labile ester thereof (referred to hereinafter as the "active ingredient"), may be administered by any route appropriate to the condition of the subject, suitable routes including oral, rectal, nasal, topical (including buccal and sublingual), vaginal and parenteral (including subcutaneous, intramuscular, intravenous. intradermal, intrathecal and epidural). It will be appreciated that the preferred route of administration may vary, for example, with the condition of the subject.

The amount of the active ingredient required for administration to a human subject will depend upon a number of factors including the condition and identity of the subject and will ultimately be at the discretion of the attendant physician. In general, a suitable, effective dose will be in the range 20 mg to 1 g per day, preferably 50 to 800 mg per day, most preferably 100 to 400 mg per day. Unless otherwise stated, all weights of the active ingredient are calculated as the weight of the parent compound and the weights would need to be increased proportionately for salts and esters.

The necessary dose of active ingredient is preferably administered as a single unit dose once daily, but may, if desired, be presented as two, three, four or more sub-doses administered at appropriate intervals throughout the day. These sub-doses may be administered in unit dosage forms containing, for example, 20 to 500 mg, preferably 100 to 400 mg, of active ingredient per unit dosage form.

While it is possible for the active ingredient to be administered alone it is preferable to present it as a pharmaceutical formulation. The formulations of the present invention comprise the active ingredient, together with one or more pharmaceutically acceptable carriers or diluents and optionally therapeutic ingredients. The carrier(s) or diluents must be "acceptable" in the sense of being compatible with the other ingredients of the formulation and not deleterious to the recipients thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant. inert diluent, preservative, disintegrant (e.g. sodium starch glycollate, cross-linked povidone, cross-liked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspension may be prepared from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The invention is illustrated by the following Examples of Pharmaceutical Compositions and Biological Data.

EXAMPLES OF PHARMACEUTICAL COMPOSITIONS

The following examples illustration pharmaceutical formulations according to the invention in which the active ingredient is 1-($\beta$-D-arabinofuranosyl)-5-propynyluracil.

Example 1

| Tablet | |
|---|---|
| Active ingredient | 100 mg |
| Lactose | 200 mg |
| Starch | 50 mg |
| Polyvinylpyrrolidone | 5 mg |
| Magnesium Stearate | 4 mg |
| | 359 mg |

Tablets are prepared from the forgoing ingredients by wet granulation followed by compression.

Example 2

Tablet Formulations

The following formulations A, B and C are prepared by wet granulation of the ingredients with a solution of povidone, followed by addition of magnesium stearate and compression.

| | mg/tablet | mg/tablet |
|---|---|---|
| Formulation A | | |
| Active ingredient | 250 | 250 |
| Lactose B.P. | 210 | 26 |
| Povidone B.P. | 15 | 9 |
| Sodium Starch Glycollate | 20 | 12 |
| Magnesium Stearate | 5 | 3 |
| | 500 | 300 |
| Formulation B | | |
| Active ingredient | 250 | 250 |
| Lactose | 150 | — |
| Avicel PH 101 ® | 60 | 26 |
| Povidone B.P. | 15 | 9 |
| Sodium Starch Glycollate | 20 | 12 |
| Magnesium Stearate | 5 | 3 |
| | 500 | 300 |
| Formulation C | | |
| | mg/capsule | |
| Active Ingredient | 100 | |
| Lactose | 200 | |
| Starch | 50 | |
| Povidone | 5 | |
| Magnesium Stearate | 4 | |
| | 359 | |

The following formulations, D and E, are prepared by direct compression of the fixed ingredients. The lactose used in formulation E is of the direct compression type.

|  | mg/capsule |
|---|---|
| Formulation D | |
| Active ingredient | 250 |
| Pregelatinised Starch NF15 | 150 |
|  | 400 |
| Formulation E | |
| Active ingredient | 250 |
| Lactose | 150 |
| Avicel ® | 100 |
|  | 500 |

The following formulation F is prepared by wet granulation of the ingredients with a solution of povidone followed by the addition of magnesium stearate and compression.

| Formulation F | |
|---|---|
|  | mg/tablet |
| Active ingredient | 500 |
| Hydroxypropylmethylcellulose (Methocel K4M Premium) ® | 112 |
| Lactose B.P. | 53 |
| Povidone B.P.C. | 28 |
| Magnesium Stearate | 7 |
|  | 700 |

Drug release takes place over a period of about 6-8 hours and is complete after 11 hours.

Example 3

A capsule formulation A is prepared by admixing the ingredients of Formulation D in Example 2 above and filling into a two-part hard gelatin capsule. Formulation B as follows is prepared in a similar manner.

| Formulation B | |
|---|---|
|  | mg/capsule |
| Active ingredient | 250 |
| Lactose B.P. | 143 |
| Sodium Starch Glycollate | 25 |
| Magnesium Stearate | 2 |
|  | 420 |

A further formulation C is prepared as follows:

| Formulation C | |
|---|---|
|  | mg/capsule |
| Active Ingredient | 250 |
| Macrogel 4000 BP | 350 |
|  | 600 |

Capsules are prepared by melting the Macrogel 4000 BP, dispersing the active ingredient in the melt, and filling the melt into a two-part hard gelatin capsule.

The following controlled release capsule formulation D is prepared by extruding the first three ingredients using an extruder, followed by spheronisation of the extrudate and drying. The dried pellets are then coated with a release-controlling membrane of ethyl cellulose and filled into a two-piece hard gelatin capsule.

| Formulation D | |
|---|---|
|  | mg/capsule |
| Active Ingredient | 250 |
| Microcrystalline Cellulose | 125 |
| Lactose BP | 125 |
| Ethyl Cellulose | 13 |
|  | 513 |

Example 4

| Injectable Formulation | |
|---|---|
| Active ingredient | 0.200 g |
| Sterile, pyrogen free phosphate buffer (pH 7.0) to | 10 ml |

The active ingredient is dissolved in most of the phosphate buffer (35°-40° C.), then made up to volume and filtered through a sterile micropore filter into a sterile 10 ml amber glass vial (type 1) and sealed with sterile closures and overseals.

Example 5

| Intramuscular Injection | |
|---|---|
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofural. The benzyl alcohol is then added and dissolved, and water added to 3 ml. The mixture is then filtered through a sterile micropore filter and sealed in sterile 3 ml glass vials (type 1).

Example 6

| Syrup Suspension | |
|---|---|
| Active ingredient | 0.2500 g |
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dissolved. In the glycerol is dispersed the thickener (dispersible cellulose). The two dispersions are mixed and made up to the required volume with the purified water. Further thickening is achieved as required by extra shearing of the suspension.

Example 7

| Suppository | |
|---|---|
|  | mg/suppository |
| Active ingredient (63 μm)* | 250 |
| Hard Fat, BP (Witepsol H15 - Dynamit Nobel) ® | 1770 |

-continued

| Suppository | |
|---|---|
| | mg/suppository |
| | 2020 |

*The active ingredient is used as a powder wherein at least 90% of the particles are of 63 μm diameter or less.

One fifth of the Witepsol H15 is melted in a steam-jacketed pan at 45° C. maximum. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 μm stainless steel screen and, with continuous stirring, allowed to cool to 40° C. At a temperature of 38°-40° C., 2.02 g aliquots of the mixture are filled into suitable plastic moulds and the suppositories allowed to cool to room temperature.

Example 8

| Pessaries | |
|---|---|
| | mg/pessary |
| Active ingredient 63 μm | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

BIOLOGICAL DATA

A. Cynomolgus Monkeys

The effect of 1(β-D-arabinofuranosyl)-5-propynyluracil in the cynomolgus monkey may be regarded as predictive of its effect in man. 1(β-D-arabinofuranosyl)-5-propynyluracil was administered by gavage to groups of three male (sexually mature) and three female cynomolgus monkeys, twice daily (6 hour interval between doses) to give total doses of 0, 25, 50, 100 and 500 mg/kg/day for 28 days. An additional two male and two female animals were dosed at 0 and 500 mg/kg/day and were then allowed a two week treatment-free period to assess reversibility. Blood samples were obtained at selected intervals at the beginning and end of the study for biochemical analysis.

Total cholesterol levels were consistently reduced to 70% of pre-dose values from Day 3 in animals dosed at 100 and 500 mg/kg/day and from Day 7 in animals dosed at 25 and 50 mg/kg/day. Cholesterol levels remained lowered at all dose levels until the end of the study, but were restored to pre-dose values 7 days after completion of treatment.

B. Human Volunteers

Three groups of six young human volunteers were subjected to a cross over study in which each group received either 25 mg, 50 mg or 100 mg of 1(β-D-arabinofuranosyl)-5-propynyluracil twice daily for 10 days and an identical placebo for the same period. The results showed a downward trend in mean plasma cholesterol concentration as follows:

| | Mean Plasma Cholesterol Level | |
|---|---|---|
| Dosage Regimen | Before Treatment | After Treatment |
| 25 mg twice daily | 5.0 mmol/l | 4.9 mmol/l |
| 50 mg twice daily | 4.9 mmol/l | 4.3 mmol/l |
| 100 mg twice daily | 5.1 mmol/l | 4.7 mmol/l |

The effects appeared to be predominantly on the LDL cholesterol fraction and there was no change in HDL cholesterol. The results provide no evidence that the maximum response has been achieved although measurement of plasma concentration of 1-(β-D-arabinofuranosyl) -5-propynyluracil suggested that the higher the peak plasma concentration of 1(β-D-arabinofuranosyl)-5-propynyluracil, the greater the fall in plasma cholesterol level. No effect was noted on plasma triglyceride levels.

We claim:

1. A method of lowering an elevated serum cholesterol level in a human having said elevated serum cholesterol level which comprises administering to said human an effective elevated serum cholesterol lowering amount of the compound 1(β-D-arabinofuranosyl) -5-propynyluracil or a pharmaceutically acceptable salt or labile ester thereof.

2. A method of lowering an elevated serum cholesterol level in a monkey having said elevated serum cholesterol level comprising administering to said monkey an effective elevated serum cholesterol lowering amount of the compound 1-(β-D-arabinofuranosyl) -5-propynyluracil or a pharmaceutically acceptable salt or labile ester thereof.

* * * * *